US00PP23371P2

(12) United States Plant Patent
Yates

(10) Patent No.: US PP23,371 P2
(45) Date of Patent: Jan. 29, 2013

(54) ***BEGONIA* PLANT NAMED 'YAMOON'**

(50) Latin Name: ***Begonia* hybrid**
Varietal Denomination: YAMOON

(76) Inventor: Frederic C. Yates, Congleton (GB)

( * ) Notice: Subject to any disclaimer, the term of this patent is extended or adjusted under 35 U.S.C. 154(b) by 0 days.

(21) Appl. No.: 13/385,940

(22) Filed: Mar. 14, 2012

(51) Int. Cl.
*A01H 5/00* (2006.01)

(52) U.S. Cl. ..... Plt./343
(58) Field of Classification Search ..... Plt./343
See application file for complete search history.

*Primary Examiner* — June Hwu
*Assistant Examiner* — Louanne Krawczewicz Myers
(74) *Attorney, Agent, or Firm* — Penny J. Aguirre

(57) ABSTRACT

A new cultivar of hybrid *Begonia* named 'YAMOON', characterized by its large, single yellow flowers with broad ovate-shaped tepals, its spreading and upright habit, its numerous basal shoots, its vigorous growth habit and its ease of vegetative propagation.

2 Drawing Sheets

Botanical classification: *Begonia* hybrid.
Cultivar designation: 'YAMOON'.

RELATED APPLICATIONS

This application is co-pending with U.S. Plant Patent applications filed for cultivars derived from the same breeding program entitled *Begonia* Plant Named 'YABOS' (U.S. Plant Pat. No. 20,093), *Begonia* Plant Named 'YABON' (U.S. Plant Pat. No. 22,802), *Begonia* Plant Named 'YASPED' (U.S. Plant Pat. No. 22,412), and *Begonia* Plant Named 'YADEV' (U.S. Plant Pat. No. 21,852).

BACKGROUND OF THE INVENTION

The present invention relates to a new and distinct cultivar of *Begonia* plant, botanically of hybrid origin and known as *Begonia* 'YAMOON' and will be referred to hereafter by its cultivar name, 'YAMOON'.

The new cultivar was derived from a controlled breeding program conducted by the Inventor at his nursery in Congleton, Cheshire, U. K. The overall purpose of the breeding program established in 2003 is to make selections of *Begonia* plants with compact plant habits suitable for container use combined with superior flower performance and productive stock plants for propagation. 'YAMOON' was selected in the Inventor's greenhouse in July of 2008 as a single unique plant from amongst the seedlings derived from a cross made in winter of 2008 between two unnamed, proprietary plants of the Inventor as the parents.

Asexual reproduction of the new cultivar was first accomplished by vegetative terminal stem cuttings in Congleton, Cheshire, U. K. in July of 2008 by the Inventor. It has been determined that the characteristics of this cultivar are stable and are reproduced true to type in successive generations.

SUMMARY OF THE INVENTION

The following traits have been repeatedly observed and represent the characteristics of the new cultivar, which in combination distinguish 'YAMOON' as a new and distinct cultivar of *Begonia*.

1. 'YAMOON' exhibits large, single yellow flowers with broad ovate-shaped tepals.
2. 'YAMOON' exhibits a spreading and upright habit.
3. 'YAMOON' readily produces numerous basal shoots.
4. 'YAMOON' exhibits a vigorous growth habit and performs well under typical production practices; a trait that is unusual for yellow flowered *Begonia* plants that are vegetatively propagated.

The male parent of 'YAMOON' differs from 'YAMOON' in having flowers that are rose salmon in color with narrower tepals. The female patent of 'YAMOON' differs from 'YAMOON' in having smaller flowers with tepals that are less broad and in being more freely branched. 'YAMOON' can be compared to cultivars from the same breeding program; 'YABOS', 'YABON', 'YASPED', and 'YADEV'. 'YABOS' differs from 'YAMOON' in having crimson colored flowers. 'YABON' differs from 'YAMOON' in having semi-double yellow flowers. 'YASED' differs from 'YAMOON' in having a more pendulous plant habit and in having dark red flowers. 'YADEV' differs from 'YAMOON' in having red flowers and in having a less compact habit with longer internodes on its branches.

BRIEF DESCRIPTION OF THE DRAWING

The accompanying colored photographs illustrate the overall appearance and distinct characteristics of the new *Begonia*. The photographs were taken near Oxford, U.K. of a 30-cm container planted with 3 plugs of 'YAMOON' and grown for 3 months.

The photograph in FIG. 1 provides a view of the habit of 'YAMOON' in bloom.

Figure 1:
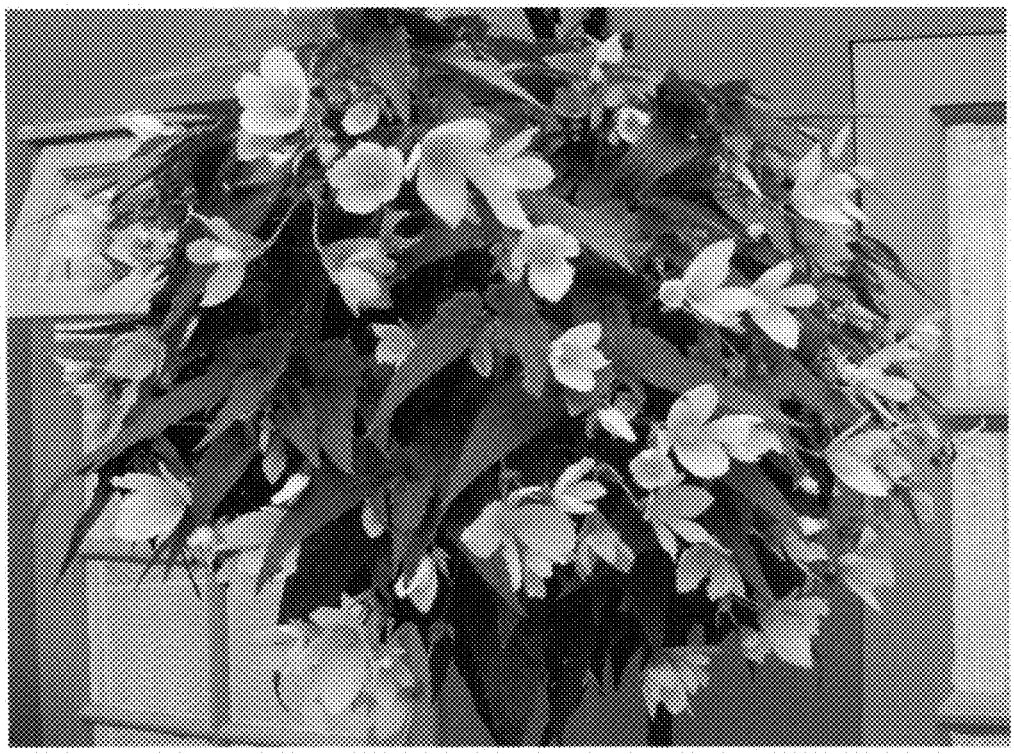
Figure 2:
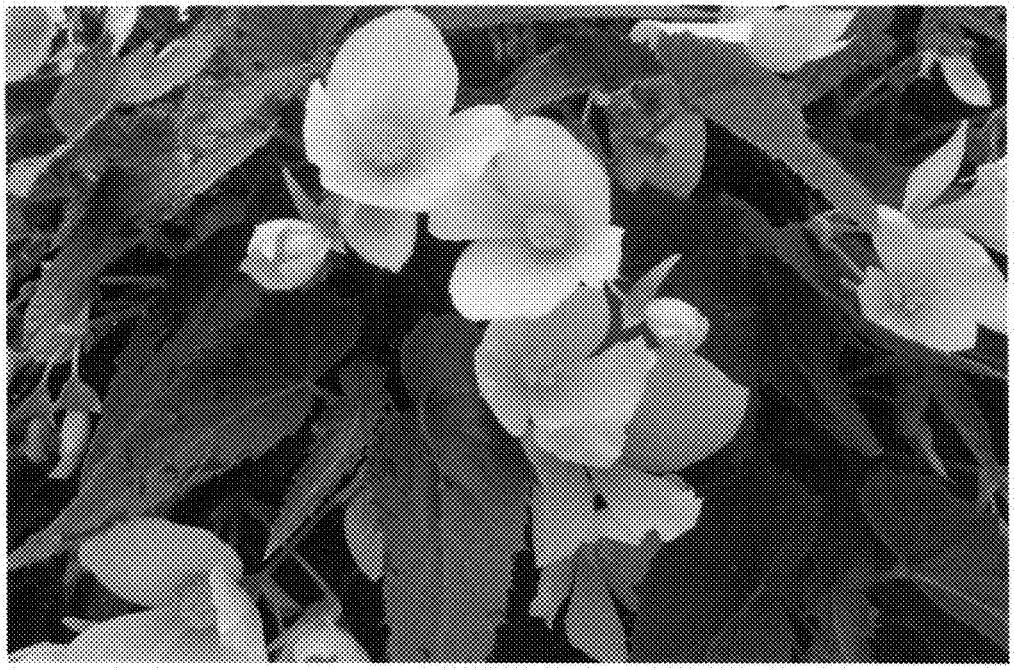

The photograph in FIG. 2 provides a view of flowers, flower buds, and leaves of 'YAMOON'.

Figure 3:
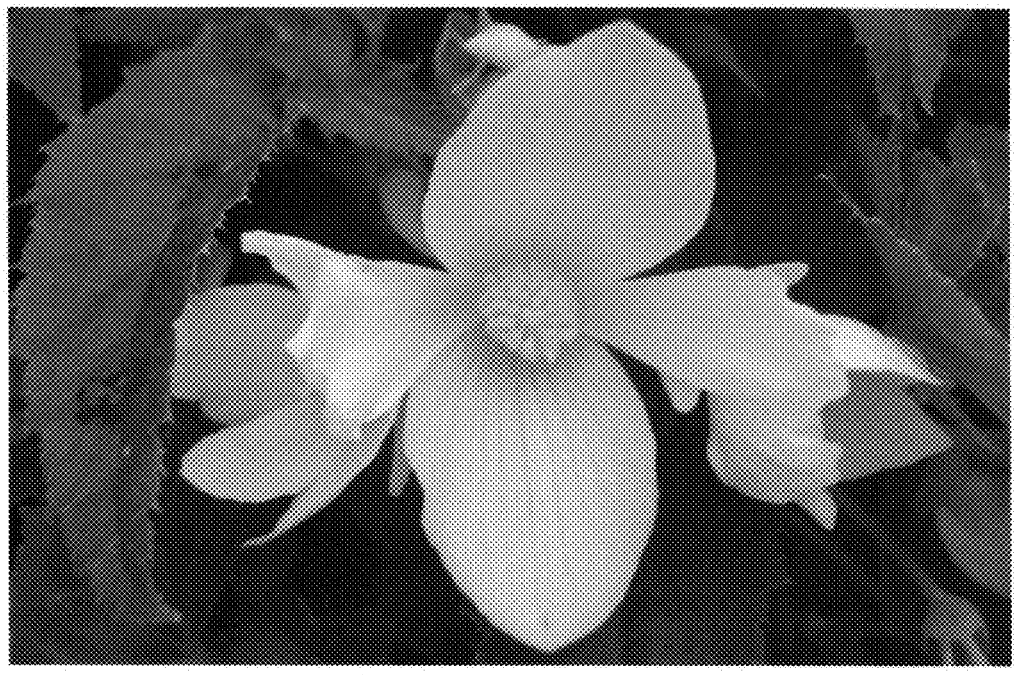

The photograph in FIG. 3 provides a close-up view of a flower of 'YAMOON'. The colors in the photograph may differ slightly from the color values cited in the detailed botanical description, which accurately describe the colors of the new *Begonia*.

DETAILED BOTANICAL DESCRIPTION OF THE PLANT

The following is a detailed description of plants of the new cultivar approximately 3 months in age as grown in 6-inch pots in an unheated greenhouse under ambient light in Liss, Hampshire, U. K. Seed pod and tuber data was taken on the same plants at 6 months of age. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General plant characteristics:

*Plant type*.—Deciduous tuberous perennial, grown primarily for use in baskets, and containers.

*Plant habit*.—Spreading and upright, freely-branching.

*Flowering period*.—From March to November in frost free areas with high light.

*Height and spread*.—Reaches about 30 cm in height and 16 cm in width.

*Cold hardiness*.—U.S.D.A. Zone 10.

*Culture*.—Grows in any commercial soil or growing media, 12 hours of light is needed and 20° C. for production in the winter months.

*Diseases and pests*.—No susceptibility or resistance to diseases or pests has been observed.

*Root description*.—Fleshy to fibrous with tubers produced for over-wintering.

*Tubers*.—Flattened, irregularly lobed, depressed in centre, an average of 4 cm in length, 3.5 cm in height and 2.5 cm in width (size varies with age of plants), surface is slightly corky, N170B in color with corky patches 177B in color.

Growth and propagation:

*Growth rate*.—Vigorous.

*Propagation*.—Vegetative terminal stem cuttings.

*Time required for root initiation*.—10 to 14 days at 22° C.

*Time required for root development*.—5 to 8 weeks to reach commercial size.

Stem description:

*Stem size*.—Average of 13 cm in length and 4 mm in width with lateral branches about 3 mm in width.

*Stem shape*.—Round, solid.

*Stem color*.—170C.

*Stem surface*.—Glabrous, lenticels absent.

*Internode length*.—Average of 2.8 cm.

*Branching habit*.—Branching from non-flowering nodes.

*Branching angle at emergence*.—About 45°.

Foliage description:

*Leaf shape*.—Lanceolate, strongly asymmetric with one side narrowly ovate, the other narrowly cordate and wider.

*Leaf division*.—Entire.

*Leaf base*.—Cordate.

*Leaf apex*.—Acuminate.

*Leaf venation*.—Pinnate, color: upper surface; 143C, lower surface; 143D.

*Leaf margins*.—Serrate with short bristles emerging from tips of the teeth.

*Leaf attachment*.—Petiolate.

*Leaf arrangement*.—Alternate.

*Leaf surface*.—Upper surface and lower surface; sparsely covered with simple pubescent translucent hairs.

*Leaf color*.—Upper surface; 137B suffused with N187A with a narrow band of 143B around veins, lower surface; 137C suffused with 184B with a narrow band of 143C around veins, new leaves on upper and lower surfaces are slightly lighter in color.

*Leaf size*.—Average of 9 cm in length and 3.2 cm in width.

*Leaf quantity*.—Average of 14 per branch (3 month-old plants).

*Leaf fragrance*.—None.

*Petioles*.—Average 1.5 cm in length and 2 mm in width, pubescent with simple hairs, color is N167C.

*Stipules*.—Broadly triangular in shape, becoming dry and papery, about 4 mm in length and 3 mm in width, 196D in color.

Flower description:

*Inflorescence type*.—2 to 3 flowered cyme produced in the axils of the upper leaves, monoecious with terminal male flowers developing before the 1 or 2 lateral female flowers.

*Peduncles*.—About 4.8 cm in length and 1.5 mm in diameter, color; 170C flushed with 40B to 40C on exposed side.

*Flower persistence*.—Self-cleaning.

*Flower type*.—Single (male and female).

*Flower fragrance*.—None.

*Flower number*.—Average of 10 per inflorescence, one inflorescence per stem (3 month-old plants).

*Flower aspect*.—Facing horizontally, hanging.

*Bracts*.—2, very broad in shape, truncate apex, bristles on margin, about 8 mm in length and 1.1 cm in width, color is 39C to 39B.

Male flowers:

*Pedicels*.—About 2.4 cm in length and 1.5 mm in width, 170C flushed with 40B to 40C in color on exposed side.

*Flower buds*.—Flattened broad ovate in shape, about 2.4 cm in length and 1.9 cm in width, color is 2D shading becoming 2C towards the base, and slightly flushed with 31D on exposed side.

*Flower size*.—About 3.4 cm in length and average 4.5 cm in width.

*Tepals*.—Outer tepals; 2 in number, ovate in shape, obtuse apex, truncate base, average of 3.1 cm in length and 2.1 cm in width, glabrous and smooth on outer and inner surface, entire margin, color: outer surface; 13D, shading to 31D, becoming 31C at the base, inner surface; apex 9D, shading to 9C at the base, becoming flushed with 31D, inner tepals; 2, occasionally 3 in number, narrow elliptic in shape, obtuse apex, cuneate base, 3.1 cm in length, 1.1 cm in width, glabrous and smooth on outer and inner surface, entire margin, color; outer surface 9D, shading to 9C at the base, inner surface 9C, shading to 9B at the base.

*Corolla form*.—Flared, tepals are un-fused.

*Stamens*.—Connate below forming tube, numerous, approximately 40 in number, broad elliptic in shape, 1.6 cm in length, 2 mm in width, 12B in color.

*Filaments*.—3 mm in length, 0.5 mm in width, 12C in color.

*Anthers*.—Broad Elliptic in shape, 1 mm in length, <1 mm in width, 17B in color.

*Pollen*.—Abundant in quantity, 14C in color.

Female flowers:

*Pedicels*.—Average 1.9 cm in length and 1.5 mm in width, color; 170C flushed with 40B to 40C on exposed side.

*Flower buds*.—Flattened ovoid in shape, about 2.2 cm in length and 1.6 cm in width, 2D, shading to 2C, towards base and slightly flushed with 31D on exposed side.

*Flower size*.—About 2.6 cm in length (excluding ovary) and 2.8 cm in width.

*Tepals*.—5 in number (3 inner and 2 outer), outer tepals; ovate in shape, acute apex, truncate base, average of 2.6 cm in length and 1.6 cm in width, glabrous and smooth on outer and inner surface, entire margin, color: outer surface; 13D, shading to 31D to 31C at the base, inner surface; 9D at apex shading to 9C at the base, flushed with 31D, inner tepals; narrowly obovate in shape, obtuse apex, cuneate base, average of 2.2 cm in length and 1.1 cm in width, glabrous and smooth on outer and inner surface surface, entire margin, color; outer surface 9D, shading to 9C at base, inner surface 9C shading to 9B at the base.

*Corolla form*.—Flared, tepals are un-fused.

*Styles*.—3 in number, cylindrical, connate at base for <1 mm, about 2 mm in length and <1 mm in diameter, 9B in color.

*Stigmas*.—Bifid in shape, stigmatic surfaces twisted around extensions of the style, lobes about 3 mm in length and <1 mm in diameter, 12A in color.

*Ovaries*.—Inferior, triangular in cross section with angles unequally winged, about 9 mm in length and 7 mm in width (excluding wings), color is 145A and becoming 150D at tips of wings.

*Seed*.—Very numerous, ovoid in shape, about 172C in color, <0.1 mm in length.

It is claimed:

1. A new and distinct cultivar of *Begonia* plant named 'YAMOON' as herein illustrated and described.

* * * * *